United States Patent
Arce Vera et al.

(10) Patent No.: US 9,238,015 B2
(45) Date of Patent: Jan. 19, 2016

(54) 4-OXO-2-PENTENOIC ACID AND CARDIOVASCULAR HEALTH

(71) Applicant: NESTEC S.A., Vevey (CH)

(72) Inventors: Francia Jacqueline Arce Vera, Lausanne (CH); Bertrand Bourqui, Murist (CH); Timo Buetler, Zurich (CH); Stephane Duboux, St-Prex (CH); Francis Foata, Lausanne (CH); Philippe Alexandre Guy, Lucens (CH); Nicolas Page, Lausanne (CH); Serge Andre Dominique Rezzi, Semsales (CH)

(73) Assignee: Nestec S.A., Vevey (CH)

( * ) Notice: Subject to any disclaimer, the term of this patent is extended or adjusted under 35 U.S.C. 154(b) by 0 days.

(21) Appl. No.: 14/389,451

(22) PCT Filed: Mar. 25, 2013

(86) PCT No.: PCT/EP2013/056262
§ 371 (c)(1),
(2) Date: Sep. 30, 2014

(87) PCT Pub. No.: WO2013/144080
PCT Pub. Date: Oct. 3, 2013

(65) Prior Publication Data
US 2015/0087707 A1    Mar. 26, 2015

(30) Foreign Application Priority Data
Mar. 30, 2012 (EP) .................................. 12162363

(51) Int. Cl.
*A61K 31/19* (2006.01)
*C12N 1/20* (2006.01)
*C12P 7/40* (2006.01)
*A61K 35/745* (2015.01)
*A23L 1/30* (2006.01)

(52) U.S. Cl.
CPC . *A61K 31/19* (2013.01); *A23L 1/30* (2013.01); *A23L 1/3014* (2013.01); *A61K 35/745* (2013.01); *C12N 1/20* (2013.01); *C12P 7/40* (2013.01); *A23V 2002/00* (2013.01)

(58) Field of Classification Search
USPC ........................................................ 514/557
See application file for complete search history.

(56) References Cited

U.S. PATENT DOCUMENTS 7,799,782 B2 *   9/2010   Munson et al. ............ 514/234.5

FOREIGN PATENT DOCUMENTS

| JP | 2008208038 | 9/2008 |
| WO | 9313076 | 7/1993 |
| WO | 2006073042 | 7/2006 |

OTHER PUBLICATIONS

Kakinuma et al. "Structure-Activity Relationship and Design of an Antimutagen against the UV-Induced Mutation of *Escherichia coli*" Agric. Biol. Chem., vol. 50, 1986, pp. 625-631.

* cited by examiner

*Primary Examiner* — Rei-Tsang Shiao
(74) *Attorney, Agent, or Firm* — K&L Gates LLP

(57) ABSTRACT

The present invention relates generally to compositions with a health benefit. In particular, the invention relates to the field of cardiovascular disorders, for example, atherosclerosis, high blood pressure, coronary heart disease, myocardial infarction, angina pectoris, stroke, and heart failure. A subject matter of the invention is a composition comprising 4-oxo-2-pentenoic acid for use in the treatment or prevention of cardiovascular disorders.

16 Claims, 7 Drawing Sheets

4-OXO-2-PENTENOIC ACID AND CARDIOVASCULAR HEALTH

CROSS REFERENCE TO RELATED APPLICATIONS

The present application is a National Stage of International Application No. PCT/EP2013/056262, filed on Mar. 25, 2013, which claims priority to European Patent Application No. 12162363.1, filed Mar. 30, 2012, the entire contents of which are being incorporated herein by reference.

The present invention relates generally to compositions with a health benefit. In particular, the invention relates to the field of cardiovascular disorders, for example, atherosclerosis, high blood pressure, coronary heart disease, myocardial infarction, angina pectoris, stroke, and heart failure. A subject matter of the invention is a composition comprising 4-oxo-2-pentenoic acid for use in the treatment or prevention of cardiovascular disorders.

Cardiovascular disorders account for approximately 20% of all annual worldwide deaths, and remain the leading cause of death in both developed and developing countries (S. K. Wattanapitayakul et al., Pharmacology and Therapeutics, 89, 187-206 (2001)). Cardiovascular disorders are also a leading cause of disability in later life. Cardiovascular disorders affect the heart or blood vessels. A major cardiovascular disorder is atherosclerosis (also known as arteriosclerotic vascular disease) which is a condition in which patchy deposits of fatty material (atheromas or atherosclerotic plaques) develop in the walls of medium-sized and large arteries, leading to reduced or blocked blood flow. Atherosclerosis is one form of arteriosclerosis, which means hardening of the arteries. Arteriosclerosis interferes with the body's control of blood pressure, increasing the risk of high blood pressure. The stiffness of the arteries prevents the dilation that would otherwise return blood pressure to normal. People with high blood pressure are at a greater risk of stroke, heart attack, and kidney failure.

Where atherosclerosis affects the arteries supplying blood to the heart (coronary artery disease) this can cause chest pain (angina pectoris) or a heart attack where an area of heart muscle is destroyed (myocardial infarction). The reduction of the flow of oxygen-rich blood to the heart muscle can cause heart failure, a disorder in which the heart pumps blood inadequately, leading to reduced blood flow, back-up (congestion) of blood in the veins and lungs, and other changes that may further weaken the heart. The failure of coronary circulation to supply adequate circulation to cardiac muscle and surrounding tissue is called coronary heart disease.

Atherosclerosis that affects the arteries to the brain leads to strokes. A stroke occurs when an artery to the brain becomes blocked or ruptures, resulting in death of an area of brain tissue (cerebral infarction).

Although the major cardiovascular disorders in terms of mortality are strokes and heart attacks, cardiovascular disorders also encompass such conditions as aortic aneurysms and peripheral vascular disease and contribute to clinical conditions including renal vascular disease, vascular dementia and retinal disease. Preventing cardiovascular disorders is not just about reducing mortality, but also about preventing disability and improving quality of life.

Initial treatment for cardiovascular disorders focuses on diet and lifestyle interventions, for example increasing exercise, eating a low fat diet and stopping smoking.

A large number of compounds have been proposed for the treatment or prevention of cardiovascular disorders. These include: salicylates (WO2009/006583), statins (J. K. Liao, International Journal of Cardiology, 86, 5-18 (2002)), angiotensin-converting enzyme (ACE) inhibitors (U.S. Pat. No. 5,684,016), angiotensin II receptor blockers (EP1604664) and calcium channel blockers (EP0089167).

Unfortunately, the treatments currently available are not always entirely satisfactory, in particular in terms of the side effects which may be associated with them. It would thus be highly desirable to have additional compositions available for the treatment or prevention of cardiovascular disorders without the drawbacks of those described in the prior art. In particular, it would be highly desirable to find an effective composition whose active ingredient is obtainable from a natural source.

Consequently, it was the object of the present invention to improve the state of the art and in particular to provide an alternative composition that can be used to treat or prevent cardiovascular disorders.

The inventors were surprised to see that the object of the present invention could be achieved by the subject matter of the independent claim. The dependent claims further develop the idea of the present invention.

Accordingly, the present invention provides a composition comprising 4-oxo-2-pentenoic acid for use in the treatment or prevention of cardiovascular disorders. The composition may be not to be used as a pharmaceutical.

The present invention also provides the use of 4-oxo-2-pentenoic acid in the preparation of a composition for the treatment or prevention of cardiovascular disorders.

"Treatment" within the scope of the present invention refers to reduction, inhibition, alleviation or amelioration.

4-oxo-2-pentenoic acid has the CAS number 4743-82-2 and the following formula

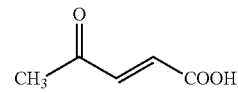

Several studies have shown that oxidative stress plays a critical role in the different forms of cardiovascular disorders, including atherosclerosis, heart failure and myocardial infarction (B. Molavi et al., Current Opinion in Cardiology 19, 488-493 (2004)). Nuclear factor (erythroid-derived 2)-like 2, also called Nrf2, is a master regulator of the antioxidant response. The transcription factor Nrf2 resides in the cytosol and is bound to an inhibitor Keap1. When bound to Keap1, Nrf2 is also rapidly degraded by the proteasome hence its low basal concentration. Upon activation by stressors (for example nitric oxide, growth factors or heavy metals) Nrf2 is released from Keap1. Nrf2 concentration increases and it translocates into the nucleus. Nrf2 then binds to the antioxidant-response element (ARE) that is present in the promoter region of genes encoding many antioxidant enzymes (Kensler T W et al., Annu Rev Pharmacol Toxicol 2007; 47:89-116).

Nrf2 is a critical regulator of cardiovascular homeostasis via the suppression of oxidative stress (J. Li et al., Expert Opinion on Therapeutic Targets, 13, 785-794 (2009)). Activation of Nrf2 by a number of compounds has been described. Polyphenols such as curcumin (US2009/0042980), resveratrol (Chen C Y et al., Biochem Biophys Res Commun 2005 Jun. 17; 331(4):993-1000), sulphoraphane (F. Elbarbry et al., Journal of Medical Plants Research, 5, 473-484, (2011)) and quercitin (Tanigawa S et al., Free Radic Biol Med 2007 Jun. 1; 42(11):1690-703) have been reported to activate Nrf2. The inventors were surprised to find that 4-oxo-2-pentenoic acid also activates Nrf2. The very low aqueous solubility of curcumin, resveratrol, sulphoraphane and quercitin affects their bio-availability. 4-oxo-2-pentenoic acid, by contrast, has good aqueous solubility.

Activation of the transcription factor nuclear factor κB (NF-κB) is associated with vascular inflammation (V. R. Baichwal et al., Current Biology, 7, R94-R96 (1997)). NF-κB is a pivotal transcription factor in chronic immune responses and inflammatory diseases (P. J. Barnes et al., The New England Journal of Medicine, 336, 1066-1078 (1997)). NF-κB is activated by numerous stimuli, including cytokines, protein kinase C activators, viruses, immune stimuli and, above all, reactive oxygen species (F. Luft, Current Hypertension Reports, 3, 61-67 (2001)). NF-κB consists of homodimers and heterodimers of Rel proteins. The predominant transactivating form of NF-κB consists of p65 and p50 heterodimers. The activation of NF-κB involves the phosphorylation and subsequent proteolytic degradation of the inhibitory protein IκB by specific IκB kinases. The free NF-κB passes into the nucleus, where it binds to κB sites in the promoter region of numerous genes involved in inflammation. Many of these genes code for cytokines, chemokines, enzymes, proteins involved in coagulation, receptors, proteinases, and adhesion molecules. These molecules contribute to the alterations in structure and mechanical properties responsible for the remodeling of resistance arteries in hypertension (H. D. Intengan et al., Hypertension, 36, 312-318 (2000)).

Inhibitors of NF-κB have been identified, such as glucocorticoids (Adcock et al., American Journal of Physiology—Cell Physiology, 268, C331-C338 (1995)) but glucocorticoids have endocrine and metabolic side effects when given systemically. Heparin has also been reported to inhibit NF-κB (WO200119376), but it has the potential side-effect of causing heparin-induced thrombocytopenia.

The inventors investigated whether 4-oxo-2-pentenoic acid inhibits NF-κB activation. Using human colonic cells and human monocytes/macrophages they found that 4-oxo-2-pentenoic acid inhibits NF-κB activation under pro-inflammatory stresses (LPS and rhTNF-α).

The inventors were surprised to find that 4-oxo-2-pentenoic acid was obtainable from natural sources, e.g. from some heat treated bacterial strains. For example, bacterial preparations of *Bifidobacterium breve* CNCM I-3865 and *Bifidobacterium breve* ATCC 15700™ both yielded 4-oxo-2-pentenoic acid when heated for 6 hours at 90° C. 4-oxo-2-pentenoic acid was found to be in the soluble fraction after centrifuging and filtering the heat treated bacterial preparations.

*Bifidobacterium breve* CNCM I-3865 was deposited with the COLLECTION NATIONALE DE CULTURES DE MICROORGANISMES (CNCM), INSTITUT PASTEUR, 25 rue du Docteur Roux, F-75724 PARIS Cedex 15, France, on Nov. 15, 2007.

*Bifidobacterium breve* ATCC 15700™ can be obtained commercially, e.g., from the American type Culture Collection (ATCC), Manassas, Va., USA, under the trademark ATCC 15700.

Consequently the present invention relates in part to a composition comprising 4-oxo-2-pentenoic acid for use in the treatment or prevention of cardiovascular disorders wherein the composition is not to be used as a pharmaceutical. A pharmaceutical is a drug or medicine that is prepared or dispensed in pharmacies and used in medical treatment (<URL: www.thefreedictionary.com/pharmaceutical/> [retrieved on 17-07-2012]). The present invention may be a food composition comprising 4-oxo-2-pentenoic acid for use in the treatment or prevention of cardiovascular disorders. The cardiovascular disorders may be selected from the group consisting of atherosclerosis, high blood pressure, coronary heart disease, myocardial infarction, angina pectoris, stroke, and/or heart failure. As discussed above, stroke and myocardial infarction (heart attack) are the major cardiovascular disorders in terms of mortality. Coronary heart disease and heart failure are also significant causes of death and debilitating ill health. Atherosclerosis is the underlying cause of many other cardiovascular disorders. Many people live with high blood pressure and regular bouts of angina pectoris, but quality of life is often affected and the people have a constant concern that these may be the prelude to strokes, heart failure or heart attacks. It would therefore be advantageous to treat or prevent atherosclerosis, high blood pressure, coronary heart disease, myocardial infarction, angina pectoris, stroke, and/or heart failure.

In the present invention the 4-oxo-2-pentenoic acid may be obtainable, for example obtained, from natural sources. Many people are concerned about the safety of materials industrially synthesised from chemical feedstock, especially when these materials are to be ingested and prefer materials obtained from natural sources.

The inventors have found that 4-oxo-2-pentenoic acid can be obtained from *Bifidobacterium breve* CNCM I-3865 and/or *Bifidobacterium breve* ATCC 15700™ (the type strain for *Bifidobacterium breve*). It is particularly advantageous to use bacteria as a source of 4-oxo-2-pentenoic acid as the production of large quantities of 4-oxo-2-pentenoic acid is feasible, for example using bioreactors. Accordingly, in the present invention the 4-oxo-2-pentenoic acid is obtainable, for example obtained, from *Bifidobacterium breve* CNCM I-3865 or *Bifidobacterium breve* ATCC 15700™.

The bacteria may be heat treated at about 60-180° C., preferably at about 80-160° C., for example at about 110-150° C. in commercial production processes. The inventors found that heat treatment at these temperatures provided a satisfactory yield of 4-oxo-2-pentenoic acid within an acceptable time. Without wishing to be bound by theory it is understood that increasing the temperature of heat treatment increases the rate of formation of 4-oxo-2-pentenoic acid but also increases the rate of its degradation. Accordingly these temperatures give a good balance between the rate of formation of 4-oxo-2-pentenoic acid and its degradation.

Typical compositions comprising 4-oxo-2-pentenoic acid may comprise 4-oxo-2-pentenoic acid in an amount of at least 1 mg/kg of the composition. Generally, it is preferred if the composition comprises 4-oxo-2-pentenoic acid in an amount of at least 10 mg/kg of the composition, more preferably between 50 mg and 50 g per kg of the composition.

The optimum amount of 4-oxo-2-pentenoic acid to be administered can be easily determined by skilled artisans.

In therapeutic applications, compositions are administered in an amount sufficient to at least partially cure or arrest the symptoms of the disorder and/or its complications. An amount adequate to accomplish this is defined as "a therapeutic effective dose". Amounts effective for this purpose will depend on a number of factors known to those of skill in the art such as the severity of the disorder and the weight and general state of the patient. In prophylactic applications, compositions according to the invention are administered to a patient susceptible to or otherwise at risk of a particular disorder in an amount that is sufficient to at least partially reduce the risk of developing a disorder. Such an amount is defined to be "a prophylactic effective dose". Again, the precise amounts depend on a number of patient specific factors such as the patient's state of health and weight. 4-oxo-2- pentenoic acid may be administered in the framework of the present invention in a therapeutic effective dose and/or in a prophylactic effective dose.

A composition of the present invention may be administered in a daily dose corresponding to between 2 μg and 20 mg of 4-oxo-2-pentenoic acid per kg of body weight, preferably between 20 μg and 2 mg of 4-oxo-2-pentenoic acid per kg of body weight, for example between 40 μg and 1 mg of 4-oxo-2-pentenoic acid per kg of body weight.

Cardiovascular disorders can affect animals as well as humans. Over 10% of all domestic animals examined by a veterinarian have some form of cardiovascular disease. Unlike diseases of many other organ systems, cardiovascular diseases generally do not resolve but almost always become more limiting and may lead to death (The Merck Veterinary Manual, 9th Edition). It is therefore an advantage to provide a composition to be administered to humans or animals. In the case of companion animals, such therapies improve the animal's overall quality of life and improve owner satisfaction. The present invention provides a composition to be administered to humans, pets or livestock.

4-oxo-2-pentenoic acid and the composition described in the present invention may be administered to adults, in particular smokers, overweight and/or obese people or people otherwise at risk of developing cardiovascular disorders. A subject is considered adult if they are of relatively mature age. Typically subjects are considered adult when they are sexually mature and capable of reproduction. According to the World Heart Federation, tobacco use increases the risks of cardiovascular disorders. The risk is especially high for people who started smoking when young, smoke heavily or are female. Passive smoking is also a risk factor for cardiovascular disorders. Physical inactivity increases the risk of heart disease and stroke by 50%.

Obesity is a major risk factor for cardiovascular disease and predisposes you to diabetes which is also a risk factor for cardiovascular disorders. Being overweight or obese are well-known disorders that represent a significant burden in our society today. "Overweight" is defined for an adult human as having a Body Mass Index (BMI) between 25 and 30. "Body mass index" is calculated as the ratio of weight in kg divided by height in meters, squared. "Obesity" is a condition in which the natural energy reserve, stored in the fatty tissue of animals, in particular humans and other mammals, is increased to a point where it is associated with certain health conditions or increased mortality. "Obese" is defined for an adult human as having a BMI greater than 30.

Another risk factor for developing cardiovascular disorders is having abnormal blood lipid levels. High total cholesterol, high levels of triglycerides, high levels of low-density lipoprotein or low levels of high-density lipoprotein cholesterol all increase the risk of heart disease and stroke.

Although the best approach regarding such modifiable risk factors as smoking and being overweight is to make lifestyle changes, it is advantageous to have compositions suitable for the treatment or prevention of cardiovascular disorders. Indeed some risk factors for developing cardiovascular disorders are not modifiable, for example: getting old, having a family history of cardiovascular disorders, being male or having African or Asian ancestry are all listed by the World Heart Federation as risk factors (Cardiovascular disease risk factors, viewed 12th Dec. 2011, http://www.world-heart-federation.org/cardiovascular-health/cardiovascular-disease-risk-factors).

The nature of the composition is not particularly limited. It may be a composition for oral, or enteral administration. The composition may be for example selected from the group consisting of a food composition, a food additive, a nutraceutical, a drink, a nutritional formulation, a tube feeding formulation, a powdered composition to be reconstituted in milk or water, and a pet food composition. Within the scope of the present invention the term nutraceutical refers to a food stuff, as a fortified food, oral supplement or dietary supplement, that provides a health benefit.

Food compositions according to the present invention are diverse in character, for example: milk, yogurt, cheese, fermented milks, milk-based fermented products, ice-creams, cereal-based products or fermented cereal-based products, milk-based powders, chilled or shelf stable beverages, confectionery, animal feed, in particular for domestic animals.

The food composition may also further comprise a protein source, a carbohydrate source, a lipid source, a mineral source and/or a vitamin source. The presence of proteins, carbohydrates, lipids, minerals and/or vitamins may have several advantages. These compounds generally contribute to the taste and mouthfeel of the final product. They also allow formulating the composition of the present invention as a complete nutritional formula, so that no additional nutrition is needed.

Compounds soluble in water have the advantage of being conveniently administered in a number of ways, including orally as solutions. The composition comprising 4-oxo-2-pentenoic acid may be water-based, for example the composition may comprise 4-oxo-2-pentenoic acid dissolved in water.

Those skilled in the art will understand that they can freely combine all features of the present invention disclosed herein. In particular, features described for different embodiments of the present invention may be combined. Further advantages and features of the present invention are apparent from the following figures and non-limiting examples.

EXAMPLE 1

Figure 1:
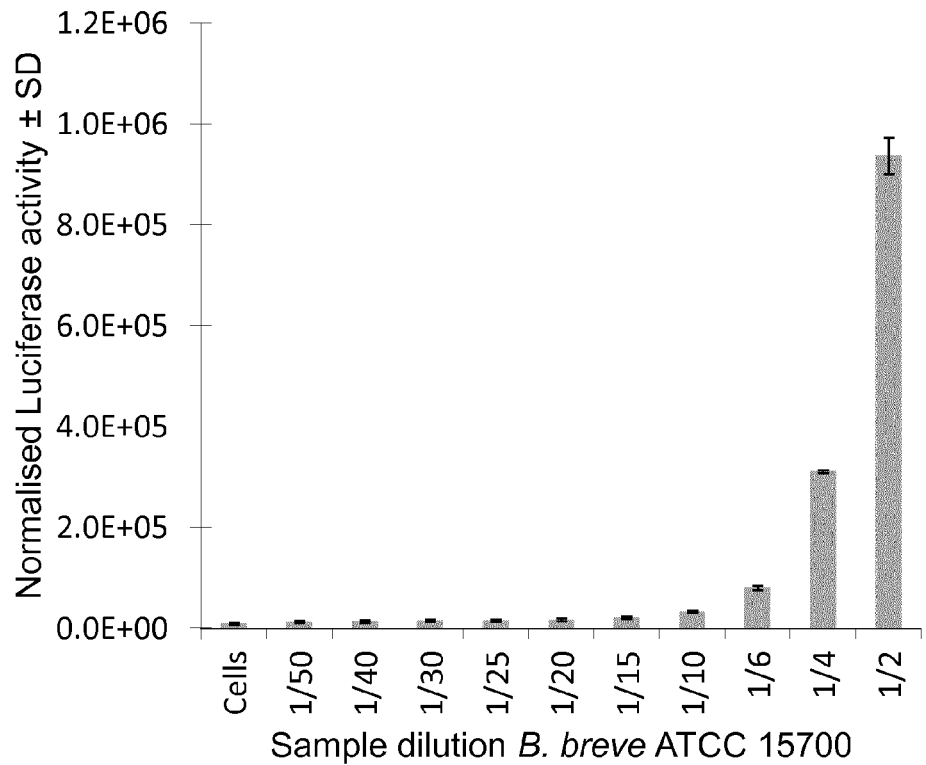
FIG. 1 shows normalized luciferase activities of crude preparations (OD 50, heated for 6 hours at 90° C.) of *Bifidobacterium breve* ATCC 15700™. The results are expressed on the y-axis as a mean±SD of technical triplicates. The x-axis values are the final dilutions of the sample.

Nrf2 Activation by 4-oxo-2-pentenoic Acid and Bacterial Fractions

Nrf2 Reporter Assay:

Activation of Nrf2 was measured using an Nrf2 reporter assay. This assay is based on the AREc32 cell line, from CRX biosciences (Dundee, Scotland), a stably transfected MCF7 (breast adenocarcinoma) cell line that contains a luciferase gene construct under the control of the ARE. Luciferase is an enzyme which digests luciferin and produces fluorescence. Anti-oxidative molecules such as Tert-butylhydroquinone (TBHQ) induce luciferase transcription via the activation of Nrf2 that binds to ARE. Luciferase activity is determined using a luciferase kit form Promega (Madison, Wis.). The luciferase activity is proportional to the activation of Nrf2.

Nrf2 Activation by Bacterial Fractions:

Three bacterial strains were used to investigate activation of Nrf2 by microorganisms: *Bifidobacterium breve* CNCM I-3865 (NCC2950), *Bifidobacterium breve* CNCM I-3914 (NCC466) and *Bifidobacterium breve* ATCC 15700™ (NCC2791). *Bifidobacterium breve* CNCM I-3914 was deposited with the COLLECTION NATIONALE DE CULTURES DE MICROORGANISMES (CNCM), INSTITUT PASTEUR, 25 rue du Docteur Roux, F-75724 PARIS Cedex 15, France, on Feb. 5, 2008.

For each strain, 10 ml of MRS agar with 0.05% cystein was inoculated with 20 μl of glycerol stock and incubated overnight at 37° C. in anaerobic condition to form pre-cultures. Further cultures were then made by inoculating 10 ml of MRS with 0.05% cystein with the pre-cultures (final $OD_{600}$ adjusted at 0.1). The cultures were incubated for 16 hours at 37° C. in anaerobic conditions to form the P2 cultures. 200 ml of MRS with 0.05% cystein was inoculated with the P2 cultures (final $OD_{600}$ adjusted at 0.1) and the bottles were incubated for 16 hours at 37° C. in anaerobic conditions.

The $OD_{600}$ was measured, the cultures were centrifuged at 3300 g for 10 min and the bacterial pellets were washed two times with cold 1×PBS (Phosphate buffered saline) and normalized to OD 50 with 1×PBS.

Bacterial fractions were obtained in two ways for each bacterial strain; a "crude preparation" and a "pure preparation".

The bacterial "crude preparations" were obtained as follows. 5 ml of the OD 50 bacterial preparations were heated for 6 hours at 90° C. in a heating block (Dri-Block DB-3 heating block from Techne, Staffordshire, United Kingdom). The heated bacterial preparations were centrifuged at 3300 g for 10 min at +4° C. and the supernatants were filtered using 0.22 μm syringe filters and stored at +4° C. until further analyses.

The bacterial "pure preparations" were obtained as follows. 5 ml of the OD 50 bacterial preparations were centrifuged at 3300 g for 10 min at +4° C. and the bacterial pellets were re-suspended with 5 ml of water. The bacterial cells were disrupted using mini bead beat (MBB) apparatus in a cold room (six cycles of 90 sec at maximum speed with 10 min of pause between each cycle). The disrupted cells were centrifuged for 1 h at 3300 g at +4° C. and the pellet was re-suspended with 5 ml of 1×PBS and heated for 6 hours at 90° C. in a heating block. The heated preparations were centrifuged for 10 min at 3300 g at +4° C. The supernatants were filtered using 0.22 μm syringe filters and stored at +4° C. until further analyses.

The live bacteria counts of the "OD 50 suspensions" were determined by plating using a spotting method, and the dry weights determined using a halogen moisture analyzer (Metler-Toledo, Greifensee, Switzerland) with the following settings: drying temperature 160° C. with step-drying activated.

To determine the Nrf2 activation the samples were tested on AREc32 cells (seeded in 96 well plates) using 10 independent dilutions (1/2, 1/4, 1/6, 1/10, 1/15, 1/20, 1/25, 1/30, 1/40 and 1/50) and incubated for 24 hours at 37° C. in a 5% $CO_2$/air incubator. The luciferase activity and the cell viability (ATP measurements) were determined using the Luciferase and Cell Titer-Glo kits from Promega.

For each run the luciferase activities, measured in Relative Light Units (RLU), of all the wells were normalized with the mean of the luciferase activity of the cells only of all the plates. Among all the samples tested the normalization procedure was found not to affect the data and this observation permits the comparison of samples measured in different runs.

For each sample the Nrf2 activation was calculated as follows:
1) The Nrf2 Fold Induction:

$$NrF2 \text{ fold induction} = \frac{\text{Normalized luciferase activity of the sample}}{\text{Normalized luciferase activity of the cells}}$$

The Nrf2 fold induction is very useful for screening purposes. However the Nrf2 fold induction is a qualitative measurement only, because this calculation does not take into account the sample dilution.
2) The Luciferase Content Per Sample:

$$\left(\begin{array}{c}\text{Luciferase content}\\ \text{per sample}\end{array}\right) = \left(\begin{array}{c}\text{Normalized luciferase activity}\\ \text{of the sample dilution giving the}\\ \text{highest } Nrf2 \text{ fold induction}\end{array}\right) \times \left(\begin{array}{c}\text{Dilution factor}\\ \text{giving the highest}\\ Nrf2 \text{ fold induction}\end{array}\right)$$

The "luciferase content per sample" also reflects Nrf2 activation but can differentiate two samples activating Nrf2 at similar Nrf2 fold inductions since this calculation takes into account the sample dilution.

The luciferase content per sample allows a semi quantification of the Nrf2 activation by reflecting the amount of the Nrf2 activating molecule.

TABLE A

Normalized luciferase activities and calculation of "luciferase content per sample" for crude preparations (OD 50, heated for 6 hours at 90° C.) of Bifidobacterium breve ATCC 15700 ™
Bifidobacterium breve ATCC 15700
Normalized luciferase content of the cells = 9583

| Sample dilution | 1/2 | 1/4 | 1/6 | 1/10 | 1/15 | 1/20 | 1/25 | 1/30 | 1/40 | 1/50 |
|---|---|---|---|---|---|---|---|---|---|---|
| Normalized luciferase | 9.37E5 | 3.11E5 | 8.02E4 | 3.28E4 | 2.15E4 | 1.72E4 | 1.54E4 | 1.52E4 | 1.41E4 | 1.32E4 |
| Dilution factor | 2 | 4 | 6 | 10 | 15 | 20 | 25 | 30 | 40 | 50 |
| Nrf2 fold induction | 97.8 | 32.5 | 8.4 | 3.4 | 2.2 | 1.8 | 1.6 | 1.6 | 1.5 | 1.4 |

Luciferase content per sample = 9.37E5 × 2 = 1.87E6
(The scientific notation 9.4E5 is equivalent to $9.4 \times 10^5$)

TABLE B

Normalized luciferase activities and calculation of "luciferase content per sample" for crude preparations (OD 50, heated for 6 hours at 90° C.) of Bifidobacterium breve CNCM I-3865
Bifidobacterium breve CNCM I-3865
Normalized luciferase content of the cells = 9583

| Sample dilution | 1/2 | 1/4 | 1/6 | 1/10 | 1/15 | 1/20 | 1/25 | 1/30 | 1/40 | 1/50 |
|---|---|---|---|---|---|---|---|---|---|---|
| Normalized luciferase | 1.16E3 | 1.46E3 | 2.62E3 | 1.24E4 | 1.05E6 | 5.19E5 | 1.04E6 | 8.30E5 | 3.37E5 | 1.87E5 |
| Dilution factor | 2 | 4 | 6 | 10 | 15 | 20 | 25 | 30 | 40 | 50 |
| Nrf2 fold induction | 0.1 | 0.2 | 0.3 | 1.3 | 10.9 | 54.1 | 108.3 | 93.4 | 35.1 | 19.5 |

Luciferase content per sample = 1.04E + 06 × 25 = 2.60E + 07

Figure 2:
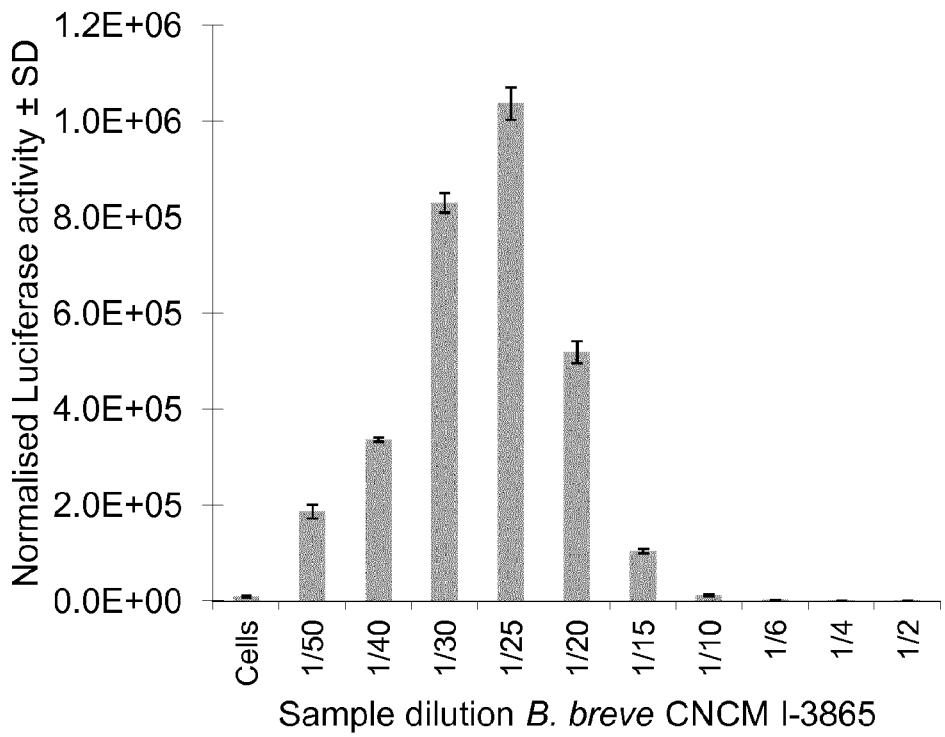
FIG. 2 shows normalized luciferase activities of crude preparations (OD 50, heated for 6 hours at 90° C.) of *Bifidobacterium breve* CNCM I-3865. The results are expressed on the y-axis as a mean±SD of technical triplicates. The x-axis values are the final dilutions of the sample.

As illustrated in tables A and B, both crude preparations of B. breve ATCC 15700™ and B. breve CNCM I-3865 have similar maximum Nrf2 induction but different luciferase content/sample values. The difference in luciferase content per sample values reflect their corresponding Nrf2 activation patterns (see FIGS. 1 and 2).

In contrast Bifidobacterium breve CNCM I-3914 did not significantly activate Nrf2, see comparison table C.

TABLE C

Comparison of results from the three different Bifidobacterium breve strains - crude preparation.

| B. breve strain code | cfu/ml | Dry weight (mg/ml) | Normalized luciferase activity | Dilution factor giving the highest Nrf2 fold induction | Nrf2 fold induction | Luciferase content per sample |
|---|---|---|---|---|---|---|
| CNCM I-3865 | 2.5E10 | 24.8 | 1.04E6 | 25 | 108.3 | 2.60E7 |
| ATCC 15700 | 1.7E10 | 23.2 | 9.37E5 | 2 | 97.8 | 1.87E6 |
| CNCM I-3914 | 1.8E10 | 24.1 | 3.06E4 | 2 | 3.2 | 6.12E4 |

TABLE D

Comparison of results from the three different
*Bifidobacterium breve* strains - pure preparation.

| B. breve strain code | cfu/ml | Dry weight (mg/ml) | Normalized luciferase activity | Dilution factor giving the highest Nrf2 fold induction | Nrf2 fold induction | Luciferase content per sample |
|---|---|---|---|---|---|---|
| CNCM I-3865 | 2.5E10 | 24.8 | 8.00E5 | 40 | 106 | 3.20E7 |
| ATCC 15700 | 1.7E10 | 23.2 | 6.55E5 | 6 | 68.4 | 3.93E6 |
| CNCM I-3914 | 1.8E10 | 24.1 | 2.42E4 | 2 | 2.5 | 4.84E4 |

Nrf2 Activation by 4-oxo-2-pentenoic Acid 4-oxo-2-pentenoic acid (Alfa Aesar—reference L02185) was tested in the Nrf2 reporter assay. Different doses of 4-oxo-2-pentenoic acid were applied on AREc32 cells for 24 h and then the luciferase activity was quantified as described above. The cell viability was also measured using a cell Titer-Glo kit (ATP quantification).

Figure 3:
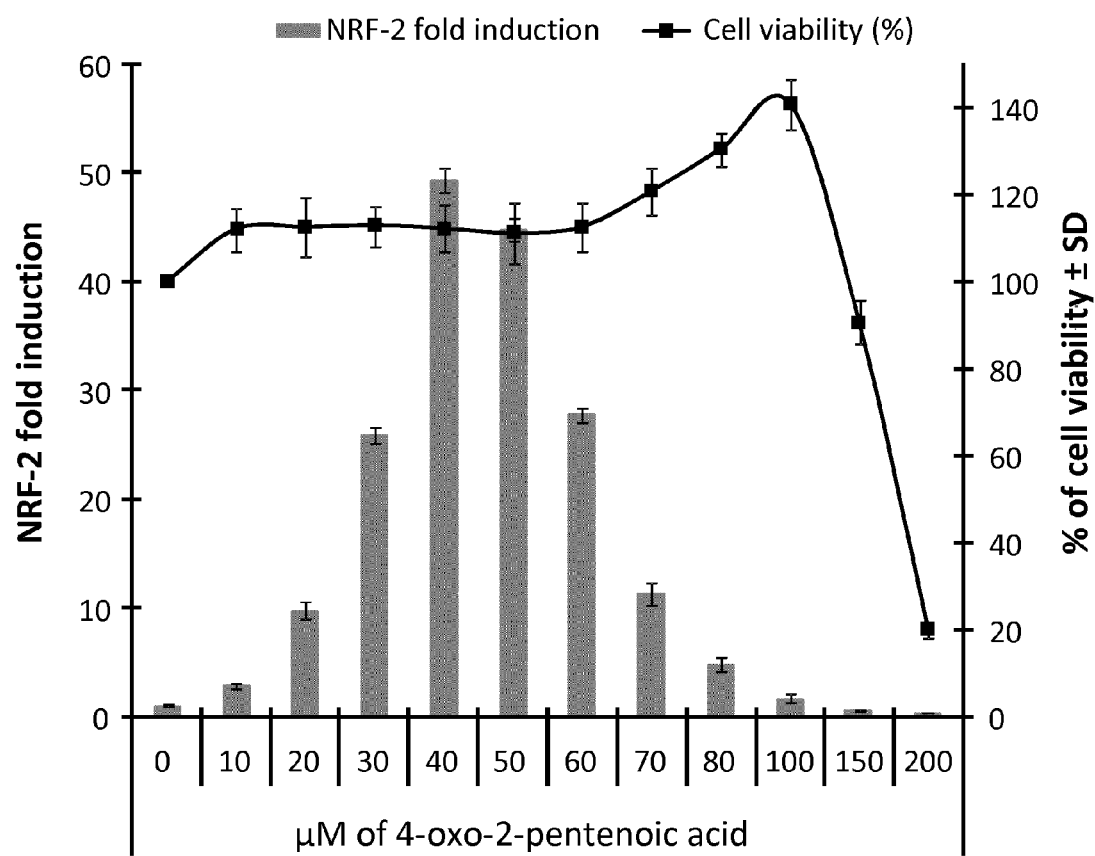
FIG. 3 shows Nrf2 induction-fold (bars) and percentage of cell viability (lines) of AREc32 cells incubated with of a dose range of 4-oxo-2-pentenoic acid from 0 to 200 μM. The Nrf2 fold inductions are ratios between the luciferase activity (RLU) of the AREc32 cells in the presence of 4-oxo-2-pentenoic acid and the basal luciferase activity of the unexposed cells. The cell viability, measured by ATP quantification, is expressed as relative percentages of control (untreated) cells. The results are expressed as means of technical triplicates±SD and are representative of four independent experiments.
Figure 4:
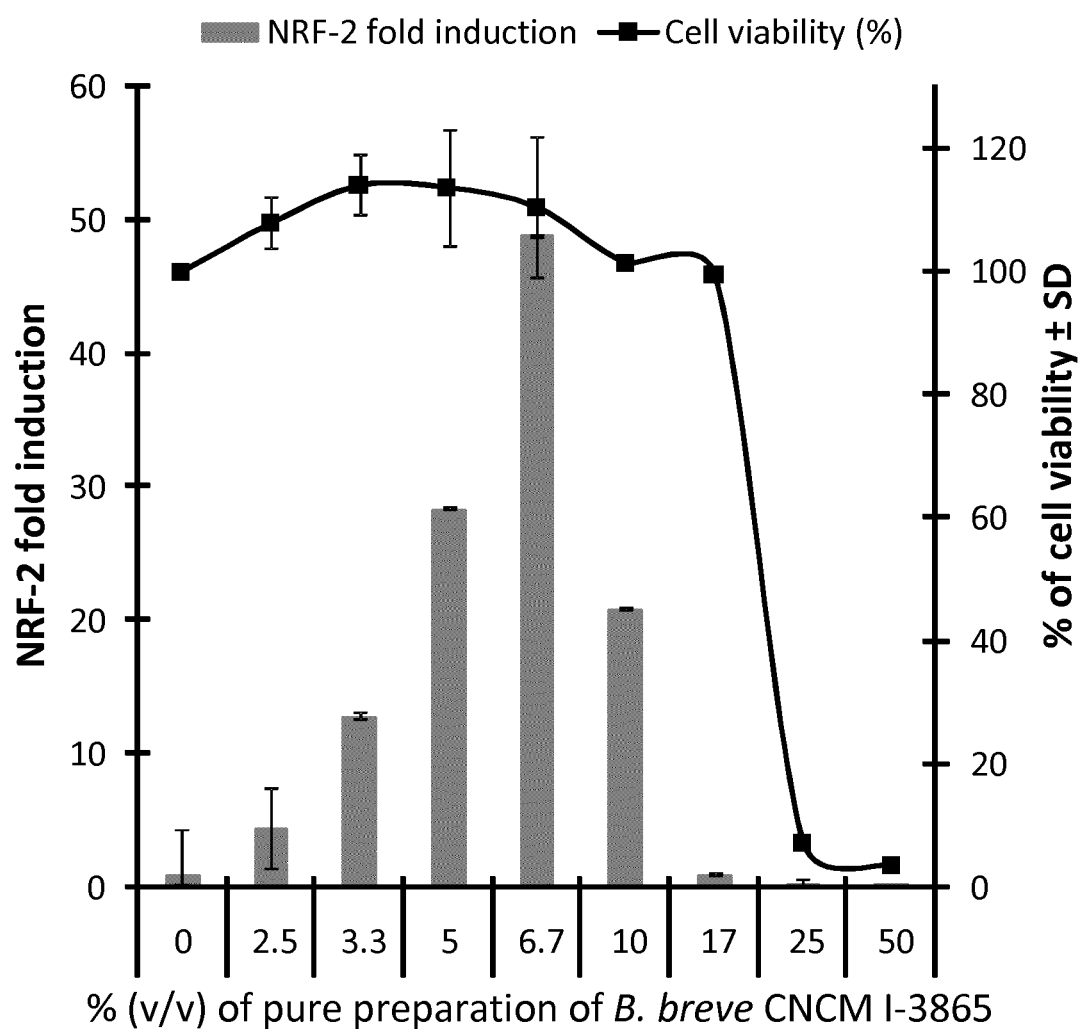
FIG. 4 shows Nrf2 induction-fold (bars) and percentage of cell viability (lines) of AREc32 cells incubated with of a dose range of a "pure preparation" of *Bifidobacterium breve* CNCM I-3865 from 2.5 to 50% v/v. Other details as for FIG. 3.

As shown in FIG. 3, the 4-oxo-2-pentenoic acid molecule was found to strongly activate Nrf2 in a dose dependent manner. The viability of AREc32 cells was not affected by 4-oxo-2-pentenoic acid at doses lower than 70 µM. The optimal dose of Nrf2 activation was around 40-50 µM. For comparison, FIG. 4 shows that a bacterial fraction of *Bifidobacterium breve* CNCM I-3865 activates Nrf2 in a similar manner.

EXAMPLE 2

Inhibition NF-κB Activation by 4-oxo-2-pentenoic Acid (Anti-Inflammatory Effect)

The inventors evaluated the capability of 4-oxo-2-pentenoic acid to inhibit NF-κB activation under pro-inflammatory stresses (LPS and rhTNF-α). Two in-vitro systems were used: human colonic cells (HT-29 clone 34) and human monocytes/macrophages (THP-1 blue cells).

HT-29 Clone 34

The human colonic adenocarcinoma HT-29 clone 34 cell line (passage 42-50) are adherent cells stably transfected with a NF-κB/SEAP reporter plasmid. They were cultured in DMEM high glucose (4.5 g/L) (Invitrogen) containing 1% of stable L-glutamine and supplemented with 10% of heat inactivated (one hour at 56° C.) Foetal Calf Serum (FCS) (Bioconcept, Allschwil, Switzerland), 1% of Penicillin/Streptomycin (Sigma) and 500 µg/ml of Geneticin (PAA, Pasching, Austria) at 37° C. in a 5% CO2/air incubator. Culture medium was renewed every two days until the cell monolayer reached ~90% confluence. Cells were sub-cultured using 1× Trypsin/EDTA (Sigma).

10000 cells/well were seeded in 200 µl of culture medium in flat bottom white border 96 well plates (Greiner Bio One, Kremsmuenster, Austria). After 3-4 days of culture (i.e. cells reaching ~70-80% confluence), culture medium was removed and 180 µl of experimental medium (DMEM high glucose supplemented with 50 mM of HEPES and 5% of human milk, as a source of sCD14 and LPS Binding Protein (LBP), for LPS stimulation only) containing (or not) dose ranges of 4-oxo-2-pentenoic acid (3 to 400 µM) were added to the cells and the plates were pre-incubated for 4 hours at 37° C. in a 5% CO2/air incubator. 20 µl of experimental medium containing (or not) LPS 055:B5 or rhTNF-α (100 and 10 ng/ml final, respectively) was added and the plates were incubated for 24 hours at 37° C. in a 5% CO2/air incubator.

Cell culture supernatants were then collected for measurement of NF-κB activity (determination of secreted alkaline phosphatase and IL-8 production) using Phosphalight (Applied Biosystems) and IL-8 singleplex (Meso Scale, Gaithersburg, Md.) kits, respectively.

Cell viability was determined by measuring ATP using Cell Titer-Glo kit (Promega). Briefly, remaining adherent HT-29 clone 34 cells were incubated for 10 min at room temperature under horizontal shaking (250 rpm) with 120 µl of Cell Titer-Glo reagent (pre-diluted twice in 1×PBS) and the luminescence was measured using Polarstar microplate reader (BMG, Offenburg, Germany) for 1000 ms with a gain value set to 3500.

In the absence of LPS no NF-κB activity was observed (based on SEAP or IL-8 detection) in cell culture supernatants of HT-29 clone 34 cells incubated with 4-oxo-2-pentenoic acid at the doses tested.

Figure 5:
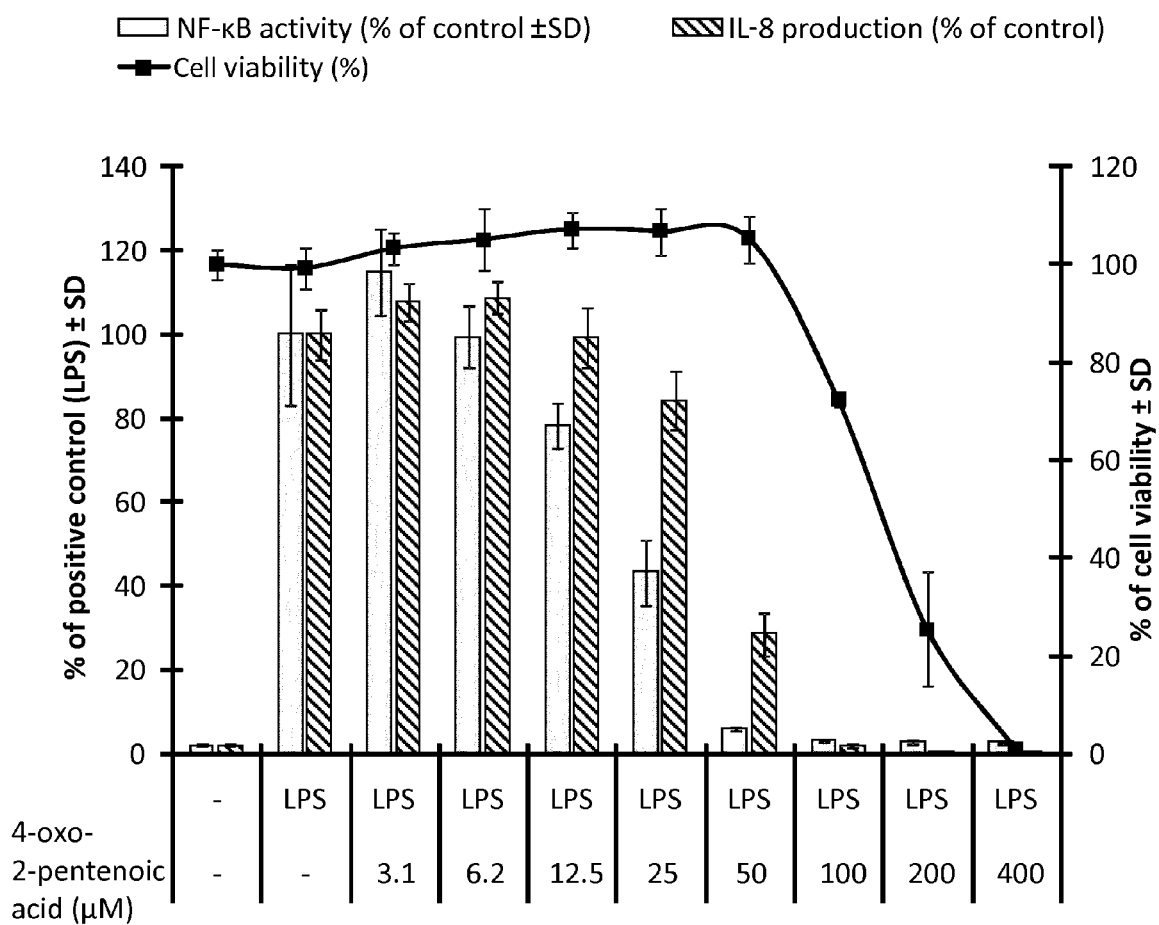
FIG. 5 shows NF-κB activity estimated by the production of SEAP (solid bars) and IL-8 (striped bars) measured in supernatant of HT-29 clone 34 cells stimulated with LPS. The cell viability is shown with a line. The cells were exposed to a dose range of 4-oxo-2-pentenoic acid. Results are expressed as means±SD of two independent experiments performed in technical triplicates.

Measurements of the cell viability of the HT-29 clone 34 cells showed a decrease in cell viability at doses of 4-oxo-2-pentenoic acid higher than ~50 µM (FIG. 5).

When inflammation response is trigged by LPS, 4-oxo-2-pentenoic acid inhibits NF-κB activity in a dose dependent manner (FIG. 5). 4-oxo-2-pentenoic acid impacted on both SEAP and IL-8 secretion, the best inhibition being with 50 µM 4-oxo-2-pentenoic acid). Similar results, although less pronounced, were observed with cells stimulated with rhTNF-α.

THP-1 Blue

Human monocytes/macrophages THP-1 blue cells (passage 16-20) (Invivogen, Toulouse, France) were cultured in modified RPMI medium (ATCC, Manassas, Va.) containing 1 mM of sodium pyruvate, 2 mM of L-glutamine, 4.5 g/L of glucose and 10 mM of HEPES supplemented with 10% of heat inactivated FCS (Bioconcept), 1% of Penicillin/Streptomycin (Sigma) and 500 µg/ml of Zeocin (Invivogen) at 37° C. in a 5% CO2/air incubator.

200000 cells/well were seeded in 100 µl of culture medium in 96 well flat bottom transparent plates. After 24 hours of incubation at 37° C. in a 5% CO2/air incubator, 80 µl of culture medium containing (or not) dose ranges of 4-oxo-2-pentenoic acid (5 to 200 µM) were added to the cells and pre-incubated for 5 hours at 37° C. 20 µl of culture media containing (or not) LPS 055:B5 (Sigma) (100 ng/ml final) was added and the plates were incubated for 16 hours at 37° C. in a 5% CO2/air incubator.

Cell culture supernatants were carefully transferred to 96 well-plates for NF-κB activity measurement which is proportional to the level of secreted alkaline phosphatase. Briefly, 100 µl of supernatants were mixed with 150 µl of QuantiBlue (Invivogen) in a 96 well-plates incubated for 3 h at 37° C. before OD measurements at 620 nm with Sunrise microplate reader (Tecan, Mannedorf, Switzerland). Cell viability was determined using Cell Titer-Glo kit as described above.

Figure 6:
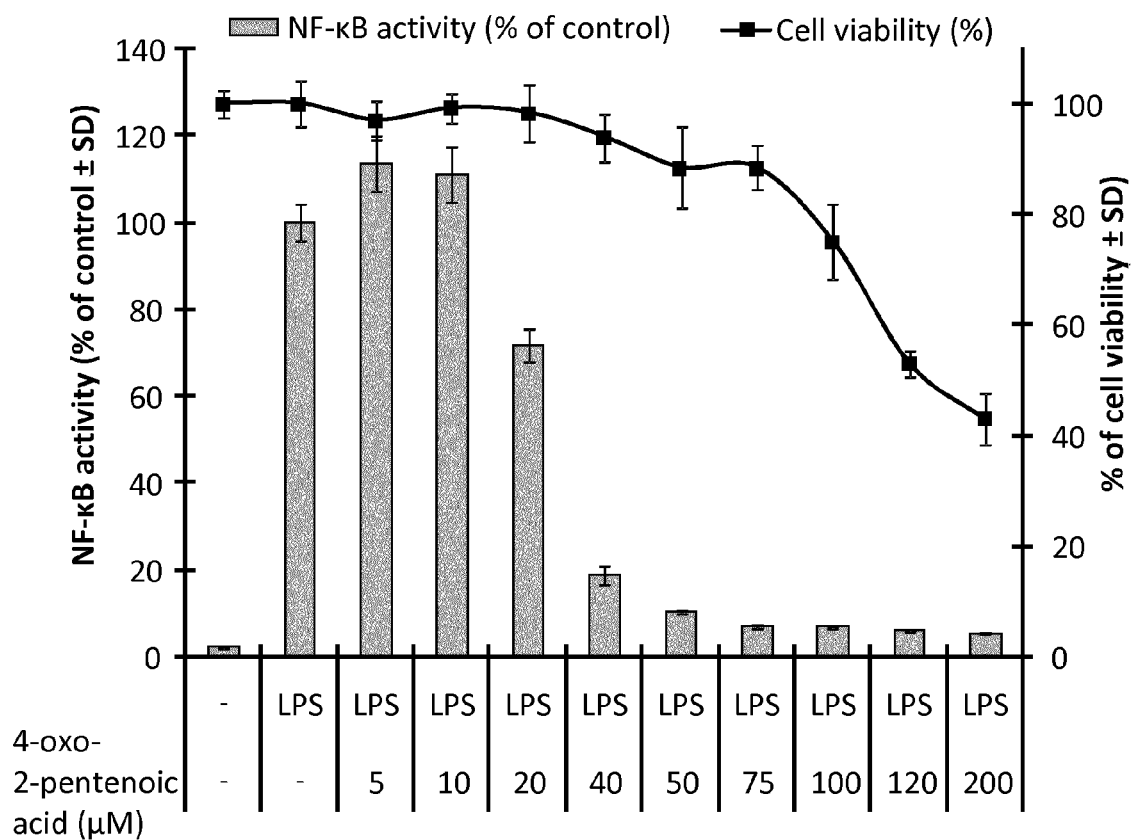
FIG. 6 shows NF-κB activity (bars) and cell viability (lines) of LPS stimulated (0.5 μg/ml) THP-1 blue cells in a presence of a dose range of 4-oxo-2-pentenoic acid for 24 h. Results are expressed as means±SD of two independent experiments performed in technical triplicates.

When stimulated with LPS, strong NF-κB inhibition was obtained in response to 4-oxo-2-pentenoic acid at doses around 40 to 75 μM. 4-oxo-2-pentenoic acid was toxic to cells at doses higher than 75 μM (FIG. 6).

The data generated with HT-29 clone 34 cells and THP-1 blue cells indicate that 4-oxo-2-pentenoic acid inhibits NF-κB activation under pro-inflammatory stresses.

EXAMPLE 3

Quantification of 4-oxo-2-pentenoic Acid by HPLC-MS/MS

In order to quantify 4-oxo-2-pentenoic acid, a high throughput analytical method involving coupling high performance liquid chromatography with electrospray ionization tandem mass spectrometry (HPLC-ESI-MS/MS) was developed.

4-oxo-2-pentenoic acid standard was purchased from Alfa Aesar (Ward Hill, USA). 4-oxo-2-pentenoic acid was found to be soluble in water to at least 20 mg/ml. 4-oxo-2-pentenoic acid standard compound was solubilised in water at a final stock solution of 10 mg/ml and further diluted in water to build a calibration curve.

HPLC-ESI-MS/MS analyses were carried out on a turbulent flow chromatography (TFC) system (Thermo Fisher, Waltham, Mass.) coupled to a 3200 Q TRAP mass spectrometer (Applied Biosystems). The analytical column used was a Hypersil Gold AQ (3×50 mm, 5 μm) purchased from Thermo Fisher (Waltham, Mass.) running at room temperature and a constant flow rate of 600 μl/min. The mobile phases were constituted with solvent A—water containing 0.05% acetic acid and B—methanol containing 0.05% acetic acid. The gradient program was: 0 min 0% B, held for 40 sec (0-0.67 min) at 0% B, ramping to 50% B in 180 sec (0.67-3.67 min), ramping from 50 to 90% B in 10 sec (3.67-3.83 min), held for 120 sec (5.83 min) at 90% B, before going back to 0% B and held for an additional 300 sec (5.83-10.83 min). The injection volume was 5 μl.

MS data acquisition was realized in electrospray negative ionization mode. MS tuning was performed by infusing a solution of 4-oxo-2-pentenoic acid standard (5 μg/ml in water) at a flow rate of 10 μl/min mixed with a HPLC flow made of solvents A and B (80/20, v:v; 0.6 ml/min) using a T-connector. Nitrogen was used for the nebulizer and curtain gases. The interface heater was activated and the block source temperature was maintained at 700° C. with a capillary voltage set at −4.5 kV. Nitrogen was also used as collision gas at a medium pressure selection. MS/MS detection was realized using the selected reaction monitoring (SRM) acquisition mode. The two most intense fragment ions were selected by scanning m/z 113→69 (collision energy of 11 eV), and m/z 113→41 (collision energy of 26 eV), using a constant dwell times of 50 ms (total scan time of 110 ms). The declustering potential was set at −29 V. Quantitative analyses were performed using the most intense SRM signal whereas the second transition was used for analyte confirmation based on appropriate area ratio calculated from standard solutions. Data processing was performed using Analyst 1.5.1 software (Applied Biosystems).

Figure 7:
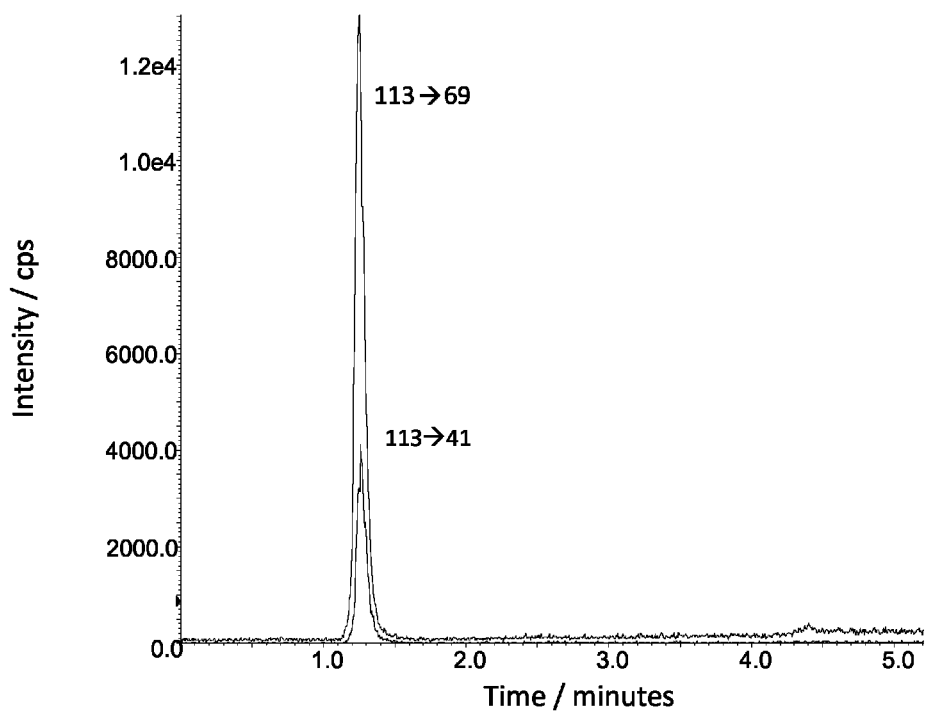
FIG. 7 shows a typical chromatogram of a 4-oxo-2-pentenoic acid standard dissolved in water. The higher SRM is associated to the transition reaction of m/z 113→69, while the lower SRM corresponds to transition reaction of m/z 113→41. The retention time is expressed in minutes (x-axis). Signal intensity (y-axis) is expressed in Cps.

Detection of 4-oxo-2-pentenoic Acid in PBS and Water by HPLC-MS/MS:

4-oxo-2-pentenoic acid was solubilised in 1×PBS or water, and the detection by HPLC-MS/MS performed as described in the previous section. The SRM associated to the transition reaction of m/z 113→69 revealed a more intense signal as compared to the SRM associated with the transition m/z 113→41 at a retention time of 1.25 min. Similar retention time for both SRMs were observed confirming the validity of the analysis, (FIG. 7). The molecule 4-oxo-2-pentenoic acid was successfully detected in both 1×PBS (data not shown) and water (FIG. 7).

Establishment of 4-oxo-2-pentenoic Acid Standard Curve:

In order to quantify precisely the amount of 4-oxo-2-pentenoic acid in bacterial fractions, standard curves were established for 4-oxo-2-pentenoic acid in simple matrices like 1×PBS or HPLC grade water. Commercial 4-oxo-2-pentenoic acid was suspended in 1×PBS and water at different doses. The HPLC-ESI-MS/MS method was then used to quantify the estimated doses of 4-oxo-2-pentenoic acid. Good linearity was observed between the quantity of 4-oxo-2-pentenoic acid (from 0.1 to 25 μg/ml) and the resulting intensities (expressed in cps) both in 1×PBS and HPLC grade water.

Quantification of 4-oxo-2-pentenoic Acid in Bacterial Fractions:

4-oxo-2-pentenoic acid was quantified in the heat treated bacterial preparations from example 1. All samples were diluted in HPLC grade water (3 dilutions/sample) before HPLC-ESI-MS/MS analysis. The results are summarized in table E.

TABLE E

Concentrations of 4-oxo-2-pentenoic acid (μg/ml) in crude and pure bacterial heated preparations (OD 50) from example 1 (6 hours of heating at 90° C.). N.D stands for "Not Detectable", below the detection limit of the method.

| Strain | Strain Code | 4-oxo-2-pentenoic acid (μg/ml) Crude preparation | 4-oxo-2-pentenoic acid (μg/ml) Pure preparation |
|---|---|---|---|
| B. breve | CNCM I-3865 | 95.3 | 126.8 |
| B. breve | ATCC 15700 | 2.1 | 16.4 |
| B. breve | CNCM I-3914 | N.D. | N.D. |

EXAMPLE 4

The Influence of Heating Temperature and Time on the Production of 4-oxo-2-pentenoic Acid from *Bifidobacterium breve* CNCM I-3865

To characterize the production of 4-oxo-2-pentenoic acid from *Bifidobacterium breve* CNCM I-3865 upon heat treatment a kinetic experiment was performed using various temperatures. The "master stock" of biomass used for this experiment was produced in bioreactors at 37° C. with MRS medium under anaerobic and pH control conditions. After the grow culture (16 h), the culture media was removed and the cells were washed two times with 1×PBS, concentrated to OD 134 (1.5E+10 cfu/ml) in 1×PBS with 10% glycerol then stored at −80° C. in 50 ml aliquots.

A "working biomass" of *Bifidobacterium breve* CNCM I-3865 was then prepared from the biomass master stock as follows: The biomass was washed two times with 1×PBS and adjusted to OD 40 in 1×PBS.

Figure 8:
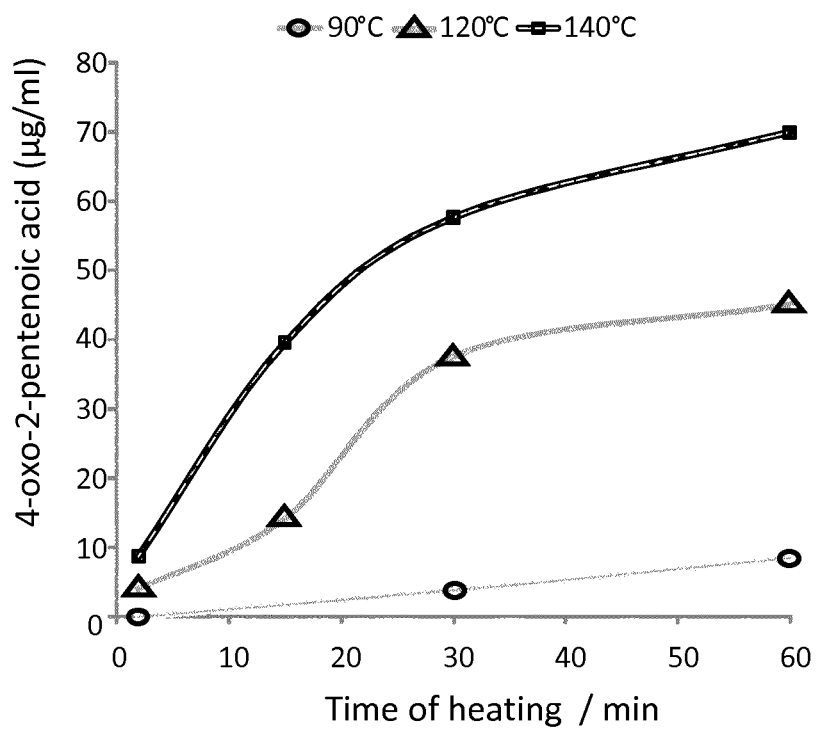
FIG. 8 shows 4-oxo-2-pentenoic acid quantification using HPLC-ESI-MS/MS of crude preparations of *Bifidobacterium breve* CNCM I-3865 (OD 40) heated for 2, 15, 30, and 60 minutes at 90° C. (indicated by circles ○), 120° C. (indicated by triangles Δ) and 140° C. (indicated by squares □).

A Temperature Heating Apparatus (THA) was used to investigate the effect of different heating times and temperatures. This system is a small scale version of typical apparatus found in production environments. Steam is used to heat up a holding tube containing cartridges of biomass. Sample temperatures of 90° C., 120° C. and 140° C. were applied for periods up to 60 minutes. 5 ml of each heat-treated biomass was then centrifuged for 10 min at 5000 g and the supernatants were filtered (0.2 μm) and the 4-oxo-2-pentenoic acid content quantified by HPLC-ESI-MS/MS. The amounts of 4-oxo-2-pentenoic acid generated are shown in FIG. 8.

The invention claimed is:

1. A method for the treatment of cardiovascular disorders, the method comprising administering a non-pharmaceutical composition comprising 4-oxo-2-pentenoic acid to a subject in need of the treatment of cardiovascular disorders, wherein the cardiovascular disorders are selected from the group consisting of atherosclerosis, high blood pressure, coronary heart disease, myocardial infarction, angina pectoris, stroke, heart failure, and combinations thereof.

2. The method in accordance with claim 1, wherein the 4-oxo-2-pentenoic acid is obtained from natural sources.

3. The method in accordance with claim 1, wherein the 4-oxo-2-pentenoic acid is obtainable from *Bifidobacterium breve* CNCM I-3865 or *Bifidobacterium breve* ATCC 15700.

4. The method in accordance with claim 3, wherein the *Bifidobacterium breve* CNCM I-3865 or *Bifidobacterium breve* ATCC 15700 was heat treated at about 60-180° C.

5. The method in accordance with claim 1, wherein the composition comprises 4-oxo-2-pentenoic acid in an amount of at least 1 mg per kg of the composition.

6. The method in accordance with claim 1, wherein the composition is administered in a daily dose corresponding to between 2 μg and 20 mg of 4-oxo-2-pentenoic acid per kg of body weight.

7. The method in accordance with claim 1, wherein the composition is administered orally or enterally.

8. The method in accordance with claim 1, wherein the composition is administered to humans, pets and livestock.

9. The method in accordance with claim 1, wherein the subject is selected from the group consisting of adult, smokers, overweight and obese people, and combinations thereof.

10. The method in accordance with claim 1, wherein the composition is selected from the group consisting of a food composition, a food additive, a nutraceutical, a drink, a nutritional formulation, a tube feeding formulation, a powdered composition to be reconstituted in milk or water, a pet food composition, and combinations thereof.

11. The method in accordance with claim 3, wherein the *Bifidobacterium breve* CNCM I-3865 or *Bifidobacterium breve* ATCC 15700 was heat treated at about 60° C. for 6 hours.

12. The method in accordance with claim 3, wherein the *Bifidobacterium breve* CNCM I-3865 or *Bifidobacterium breve* ATCC 15700 was heat treated at about 80-160° C.

13. The method in accordance with claim 3, wherein the *Bifidobacterium breve* CNCM I-3865 or *Bifidobacterium breve* ATCC 15700 was heat treated at about 110-150° C.

14. The method in accordance with claim 1, wherein the composition comprises 4-oxo-2-pentenoic acid in an amount of at least 10 mg per kg of the composition.

15. The method in accordance with claim 1, wherein the composition comprises 4-oxo-2-pentenoic acid in an amount of between 50 mg and 50 g per kg of the composition.

16. The method in accordance with claim 1, wherein the composition is administered in a daily dose corresponding to between 40 μg and 1 mg of 4-oxo-2-pentenoic acid per kg of body weight.

* * * * *